United States Patent [19]
Schwartz

[11] 4,126,133
[45] Nov. 21, 1978

[54] INTRACORPOREAL CATHETER IMPROVEMENT

[76] Inventor: Boris Schwartz, 400 Park Ave., Paterson, N.J. 07504

[21] Appl. No.: 815,207

[22] Filed: Jul. 13, 1977

[51] Int. Cl.² ............................................. A61M 5/00
[52] U.S. Cl. .................................. 128/214.4; 128/274; 137/323; 251/309
[58] Field of Search ............ 128/214 R, 214 B, 214.4, 128/274, 221; 137/323, 625.47; 251/309

[56] References Cited
U.S. PATENT DOCUMENTS

| 3,185,179 | 5/1965 | Harautuneian | 137/625.47 |
| 3,434,691 | 3/1969 | Hamilton | 128/221 X |
| 3,678,960 | 7/1972 | Leibinsohn | 251/309 X |
| 3,774,604 | 11/1973 | Danielsson | 128/214.4 |

FOREIGN PATENT DOCUMENTS

| 590,497 | 3/1925 | France | 128/274 |
| 575,559 | 4/1924 | France | 128/214.4 |

Primary Examiner—Dalton L. Truluck
Attorney, Agent, or Firm—Ralph R. Roberts

[57] ABSTRACT

There is provided a catheter having a hub portion in which a rotatable intravenous receiving member is mounted. In one position the rotatable member provides a passageway for a needle passable through the rotating portion and the hub end and extending portion of the catheter. After insertion of the catheter into the patient, the needle is withdrawn from the assembly. Before inserting the needle into the patient and then withdrawing the needle from the assembly, an end of an intravenous conductor is connected to the receiving socket in the rotating portion and placed in a fluid-flow condition or the intravenous connector can be inserted after venipuncture. After the needle is withdrawn, the rotatable portion is turned to bring the connected fluid source into flow condition to and with the catheter. A filter may be provided in the passageway of the fluid conduit in the rotatable portion.

14 Claims, 8 Drawing Figures

INTRACORPOREAL CATHETER IMPROVEMENT

CROSS REFERENCE TO RELATED PATENTS

To the extent applicable and directed to the same subject matter and problem, reference is made to my U.S. Pat. No. 3,599,637 as issued on Aug. 17, 1971 and entitled, "Intravenous Catheter Assembly." Reference is also made to my U.S. Pat. No. 3,863,632 as issued on Feb. 4, 1975 and entitled, "Intracorporeal Catheter Assembly".

BACKGROUND OF THE INVENTION

1. Field of the Invention

The classification of art as established by the United States Patent and Trademark Office is believed to place this invention in the general Class entitled, "Surgery" (Class 128) and in the subclass entitled, "dosing devices — intravenous — coaxial" (sublcass 214.4).

2. Description of the Prior Art

This apparatus provides a flexible catheter with means for determining the placement of the catheter into the vein of the patient. In addition to this embodiment there have been many attempts to provide closed systems in which the catheter, when connected to an intravenous member, may allow the withdrawal of the needle without a serious back flow of blood from the vein. Among these are my U.S. Pat. No. 3,599,637 as issued on Aug. 17, 1971 and my U.S. Pat. No. 3,863,632 as issued on Feb. 4, 1975. There is also a showing in U.S. Pat. No. 3,915,168 as issued on Oct. 28, 1975 to MONESTERE, et al. In all of these systems after the penetration of the skin and a vein is entered, the needle is withdrawn from the catheter. The intravenous feeding system in the above embodiments is connected through a socket in the catheter assembly to a tapered portion of the fluid conductor.

The present invention is directed toward providing a closed catheter system which enables the needle portion to be inserted into and through the tubular catheter portion without previous penetration of or a later withdrawal through the wall of a rubber or plastic tubing. At the same time, this assembly enables the fluid conducting tubing to be hooked up to the catheter before insertion of the needle into the patient and subsequent withdrawal of the needle from the catheter. Y-block concepts have previously been used to achieve closed systems.

In the present embodiment there is provided an auxiliary assembly which may be hooked up to an existing catheter. A slightly longer needle is used instead of the original needle. In another embodiment, the rotating intravenous member connection may be made as an integral part of the flexible catheter hub. It is to be noted that the needle in the passageway in the catheter acts as a shutoff for the flow of intravenous fluid through the catheter until the needle is withdrawn from the catheter and also prevents the spillage of blood from the catheter when the rotating member is moved into position.

In the embodiments to be fully described and shown, the present invention contemplates that the catheter with an enclosed needle may be inserted in a vein of a patient. A fluid conductor is connected to a socket portion of a rotatable portion of the apparatus. With the needle in place fluid flow through the conductor is inhibited. When this needle is withdrawn, the rotary member can be moved to a flow condition with the catheter.

SUMMARY OF THE INVENTION

The catheter assembly of this invention includes a flexible plastic tubing having its distal end tapered to assist in the penetration of the skin of the patient. This catheter is used in combination with a needle to accomplish the penetration of the skin. The other end of the catheter is attached to or is integrally molded with a conical hub portion which provides a tapered entrance into the bore of the catheter. Two concepts of the invention are shown. In one arrangement, a molding of the hub of the catheter includes forming the hub with a receiving portion in which a rotating member is mounted. This rotating member, in one condition, provides a passageway for the entry of a needle into the catheter and the withdrawal of the needle from the catheter. In another portion of the rotating member is formed a socket for the receiving of an end of a fluid conductor. A passageway through the axial portion of the rotating member when rotated into a determined position brings a passageway from the conductor into flow connection with the passageway of the catheter.

In another embodiment, a standard catheter and hub is used. A small auxiliary member is formed having an entry nozzle portion for mounting in the hub of the catheter. A needle which is slightly longer than that used in the regular catheter passes through a passageway formed in this auxiliary member and then into the passageway of the catheter to provide the assist in the penetration of the vein. This needle may also provide a cutoff for the fluid from the intravenous connection. A female socket is formed in this rotating member and is connected by a passageway extending through the rotating member. The needle in one passageway closes off the fluid conducting passageway. After the needle is withdrawn, a rotating action of approximately thirty degrees brings the fluid connection into a flow conducting condition with the catheter.

In my prior invention, as shown in U.S. Pat. No. 3,599,637, the passage of the needle through a wall of the catheter causes a possible penetration and inclusion of a portion of rubber in the tip or in the needle itself. This defect or possible objection to its use was noted. My U.S. Pat. No. 3,863,632 was directed toward providing a closed system where after the needle was withdrawn the intravenous member was in full connection without the penetration or passage of the needle through the flexible wall. The manufacturing difficulties and the reluctance of attendants to use this specially shaped catheter assembly, as well as the possibility of utilizing a filter in the flow conduit of the intravenous member, has led to the present concept.

There has been shown two specific embodiments of the catheter contoured to receive a conical semiflexible tubular member which forms the end of a feeding, injecting or drainage unit. With the catheter there is shown also a needle which is connected to a means for creating a negative pressure to determine the placement of the catheter in the body of a patient as, for example, in a vein. These specific embodiments have been shown for the purpose of illustration and description and as shown in the accompanying drawings wherein:

Figure 4:
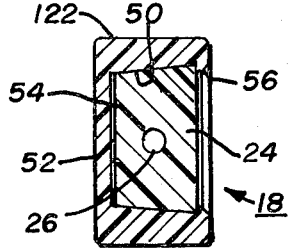
FIG. 4 represents a sectional view taken on the line 4—4 of FIG. 2.

In the following description and in the claims various details will be identified by specific means for convenience. These names, however, are intended to be generic in their application. Corresponding reference characters refer to like members in the eight figures of the drawing. The drawing accompanying and forming part of this specification discloses details of construction for the purpose of explanation of the broader aspects of the invention but it should be understood that structural details may be modified in various respects without departure from the concepts and principles of the invention.

DESCRIPTION OF THE PREFERRED EMBODIMENT

Figure 1:
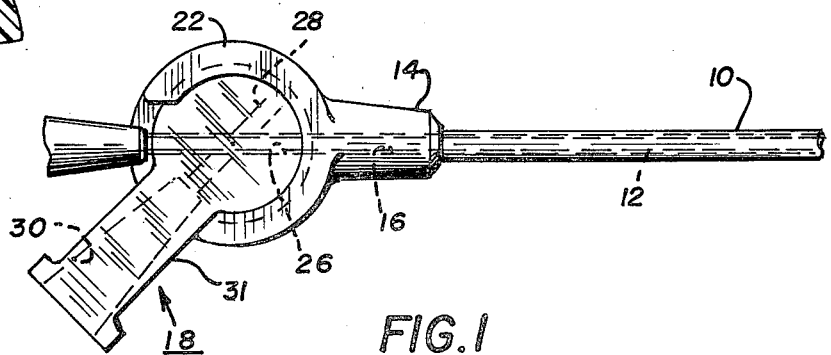
FIG. 1 represents a side view of an intracorporeal catheter assembly of this invention and showing a rotating portion with the assembly carrying a needle in the catheter and ready for venipuncture.

Referring now to the drawing and in particular to FIG. 1, it is to be noted that a flexible catheter member 10 has a needle through the reduced forward portion thereof. This needle, identified as 12, continues through the hub portion 14 and a passageway 16 into and through a rotatable member, generally identified as 18, and to and through an open exit part of this rotatable member. The rear end of the needle 12 is connected to a flash-back indicator 20. Hub 14 is contemplated to include a circular skirt retaining portion 22 which rotatably retains member 18. This rotatable member 18 includes a center circular portion 24 through and in which are formed a needle passageway 26 and a fluid conducting passageway 28. Passageway 28 terminates with and at a tapered socket portion in hub 31 which is sized to receive an end of a fluid conductor for intravenous, blood or similar purpose.

Figure 3:
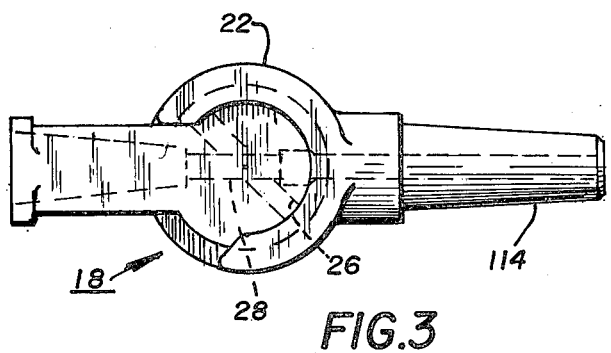
FIG. 3 represents a side view of the rotating assembly of FIG. 2 with the needle withdrawn and the rotating portion moved to a full flow connection of the fluid conductor socket and the catheter mounting end of the assembly.

It is to be noted that as turned to the position of FIG. 1, the rotatable member 18 is aligned so that needle 12 may be inserted through passageway 26, 16 and catheter 10. The rotatable member 18, no matter whether in the needle receiving portion of FIG. 1 or the fluid flow transmitting condition such as seen in FIG. 3, is in a fluid-tight mounting in the skirt portion 22 of the hub. This allows a fluid connector end to be mounted in the tapered socket 30 without fluid flow from the end of passageway 28. When the passageways 26 and 28 are connected, the presence of a needle 12 in passageway 26 inhibits a flow in passageway 28. With the rotatable member 18 turned to carry fluid to the catheter 10, the passageway 26 with the needle 12 now absent has both ends closed by the skirt 22 to prevent a fluid flow from either end of the passageway.

In the condition or position of FIG. 1, the rotatable member 18 is turned so that the needle 12 may be inserted through the passageways 26 and 16 and into the catheter 10. The needle and catheter are adapted for penetration and insertion of the catheter into the vein of the patient. The flow conductor may be inserted into the socket 30 either prior to venipuncture or after venipuncture depending upon the technicians preference. The needle 12 is then withdrawn and the rotating member 18 is moved into the position of FIG. 3 with the passageway 28 in alignment with the passageway 16 and the passageway through the catheter 10. Fluid flow then is delivered to the catheter.

EMBODIMENT OF FIGS. 2 AND 3

Figure 2:
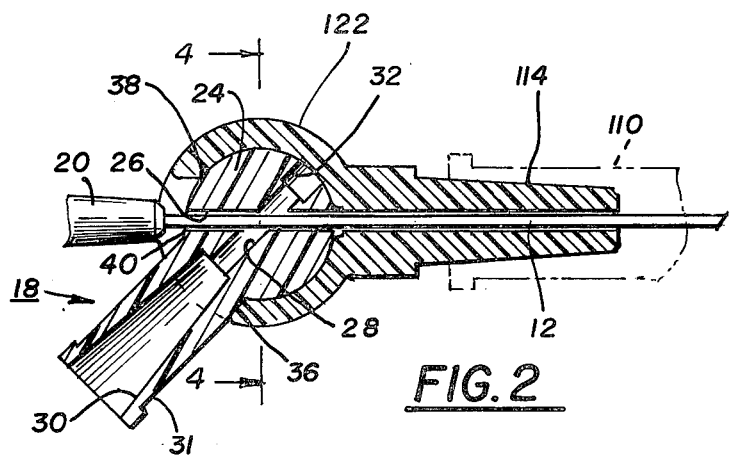
FIG. 2 represents a side view in section of an alternate embodiment and showing a rotating assembly which may be placed in the hub portion of an existing catheter and with the needle inserted through the rotating assembly and into the bore of the catheter.

In FIGS. 2 and 3, it is to be noted that the rotatable member 18 is secured in a hub portion 114 which may in turn be mounted in a hub portion of a conventional catheter and is made as an insertable unit into a catheter. The conventional catheter is shown in phantom outline and is indicated in FIG. 2 as 110. Needle 12 which has a flash-back indicator 20 on the rear portion thereof passes through a passageway 116 in a socket engaging portion 144 of the insertable member. An outer circular portion 122 retains the rotating members 18 within this receiving circular skirt portion 122. As depicted in FIG. 2, the unit is in the condition of FIG. 1 with the needle 10 passing through passageway 26 in the rotatable member 18. The end of fluid conducting passageway 28 may be formed with a recess 32 in which is carried a filter 34. A shoulder or end portion 36 on the circular skirt portion 122 provides a limiting stop for the hub 31 and its receiving socket 30. A small detent 38 is formed within the tapered recess of the member 122 and is adapted to engage and retain a mating protruding portion 40 formed on the end member 18. This detent 38 is adapted to engage and retain the rotating member in a desired alignment when the rotatable member 18 is rotated to the condition of FIG. 3. The tapered portion of the forward section 114 is adapted to fit within the tapered socket recess of a catheter having the usual catheter construction. The taper 30 in the hub section 3 is also sized to receive a tapered end of a fluid conductor, not shown.

EMBODIMENT AND ASSEMBLY OF FIG. 4

In FIG. 4 it is to be noted that the socket section 122 is formed with a tapered recess 50 with a back wall 52 which retains this socket in the formed configuration. A small space of a few thousandths of an inch, identified as 54, insures that the taper 50 matches and slidably engages a like taper formed circular hub portion 24. This rotatable member 18 is retained in the tapered recess 50 by means of a lip or ring 56 formed at the open side of the tapered recess 50.

As reduced to practice, the circular skirt portion 22 or 122 is formed with a tapered recess 50 having a retaining ring portion 56. This retaining ring may be a full ring or portions thereof forming retaining lugs. The rotatable member 18 is placed with the tapered portion arranged to mate with recess 50. The rotatable member extends about half way into the recess and the hub portion 31 is in the gap between shoulders 36 and 38.

To assemble, a push force is applied to the circular portion 24 of the rotatable member 18. The circular skirt member 22 or 122 is supported sufficiently for the rotary member 18 to be pushed into a seated condition. The filter 32 may be inserted into the rotatable member 18 at the end of passageway 28. The rotatable member is turned to the condition of FIGS. 1 or 2 and the needle 12 inserted into and through the catheter 10 for venipuncture and insertion prior to use.

EMBODIMENT AND ASSEMBLY OF FIG. 5

Figure 5:
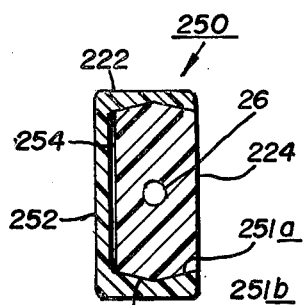
FIG. 5 represents a sectional view similar to that of FIG. 4 and showing a slightly different configuration for the seating of the rotating member in the socket portion of the rotatable receiving member.

In FIG. 5 is shown an alternate construction of the circular skirt and its recess in which is mounted a rotatable member. As depicted, a circular skirt portion 222 may have an open recess 250 which has sloped surfaces 251a and 251b. A circular portion 224 having like sloped surfaces is a snug fit in the formed recess. In a mounted condition the circular portion 224 provides a small clearance 254 between a back wall 252 in the skirt portion 222.

To assemble, the circular portion 224 is brought to and partially seated in the recess 250. In the manner of FIG. 4, the rotatable members are then pressed into a seated and rotating condition in the circular skirt retainer 222. The two sloped surfaces 251a and 252b in the skirt recess 250 are compatible with like sloped surfaces formed on the rotatable member. Selective design permits circular portion 224 to be about half way inserted into the recess before mounting pressure is required to press the rotating member into place.

CONSTRUCTION AS IN FIG. 6

Figure 6:
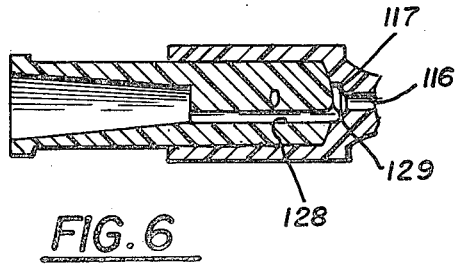
FIG. 6 represents a fragmentary sectional view taken generally on the center line of an assembly such as in FIG. 3, this view showing the conduit from the socket to the inlet for the catheter offset from the needle passageway in the rotating member.

In FIG. 6 there is shown an arrangement in which the needle passageway extends through the circular portion of the rotatable member and the fluid-flow passageway is arranged to by-pass and not intersect the needle passageway. As shown, the components of FIGS. 2 and 4 are used. The circular skirt 122 is as shown in these FIGS. but at the inner terminal end of passageway 116 a transverse recess 117 is formed. This recess does not extend to the outer or open side of the recess. The needle passageway 26 is substantially central of the circular skirt portion 122 and in alignment with bore 116.

A fluid-flow passageway 128 leads from the inner end of the tapered socket 30 in hub portion 31 and past the needle passageway 26 and terminates to provide a flow connection with transverse recess 17. An enlargement 129 of the end of the passageway 128 may be formed in the rotary member to assist in the fluid flow from passageway 128 to the catheter when the hub is turned to the condition of FIG. 3. This by-pass passageway 128 does not intersect the needle passageway so that connection of a fluid-flow tubing in socket 30 does not start a flow to and through passageway 116 until the needle is withdrawn and the rotary member turned to the condition of FIG. 3 and as shown in FIG. 6.

EMBODIMENT AND ASSEMBLY OF FIG. 7

Figure 7:
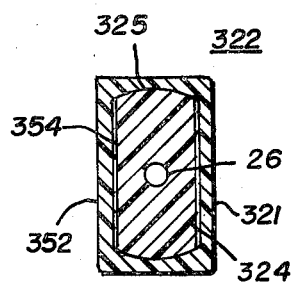
FIG. 7 represents a sectional view similar to that of FIGS. 4 and 5 but showing a different means of forming and seating the rotatable member in the rotatable receiving member.

In FIG. 7 is shown a cross section of yet another embodiment of a circular skirt and a rotatable member. As shown, a circular skirt 322 has both a front wall 321 and a rear wall 352. A rotatable member 324 is insertable into an opening between the two stop shoulders corresponding to 36 and 38, as seen in FIG. 2. Arcuate portions or surfaces 325 may be formed to provide a seating and guide of the rotatable member in the circular skirt portion 322. A small space 354 of a few thousandths of an inch may be provided on each side of the rotatable member.

It is anticipated that the rotatable member 324 is inserted through the opening in the circular skirt 322. Passageways 26 and 28 are also formed in the rotatable member and the hub 31 and socket 30 correspond to that, above described. Knob 40 and detent 38, as above described, may also be provided.

EMBODIMENT OF FIG. 8

Figure 8:
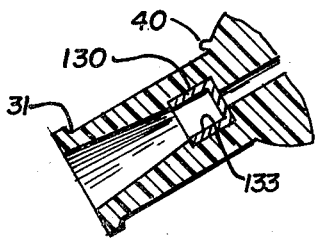
FIG. 8 represents a side view substantially similar to that of FIG. 2 and showing the rotating member, as seen in FIG. 2, with a different method for mounting a filter in the socket receiving portion.

Referring next and finally to the rotatable member, as shown in FIG. 8, it is to be noted that any of the above-described rotatable members may have hub 31 formed with a socket 130 which is formed to receive and retain the end of a fluid conductor. The socket is altered to receive a filter 133 which is cup-shaped and of rather a thin wall to allow a fluid flow at or with a low head or pressure. The passageways 26 and 28, as above described, are also provided as is knob 40.

It is to be noted that the rotatable member may be as in FIGS. 4, 5, 6, 7 and 8 or modifications thereof. The circular skirt which retains this rotatable member may be an integral part of a catheter, as in FIG. 1, or a part of an insert assembly, as shown in FIG. 2. In either arrangement, a needle 12 is inserted through the rotatable member and passageway 26 and the catheter 10. Into the socket 30 is inserted a flow conductor of conventional construction. While the rotatable member is in the position of FIGS. 1 and 2, penetration of the skin and vein is achieved. The presence of the needle in passageway 26 prevents a flow in passageway 28. With the withdrawal of the needle 12, the rotatable member is turned to the fluid-flow condition of FIG. 3. The stop shoulders 36 and 38 establish the limits of travel of hub 31. Whether or not a filter is used, as seen in FIGS. 2 and 8, the needle does not pass through a filter, rubber or plastic wall.

Turn cocks are known, as shown in French Pat. No. 575,559 published Aug. 1, 1924. Also known is the unsymmetrical assembly of my U.S. Pat. No. 3,863,632, above noted. The present invention provides apparatus that requires little instruction to the administrator and a simple turn operation brings the flow conductor into fluid flow with the catheter. The length of the needle is made to suit the length of the catheter, hub and rotatable member. The diameter of this needle is sized to accommodate the bore of the catheter and the passageway 26 which is of a similar size.

The present invention provides many advantages as, for example, this unit adapts to most commercial catheters and no change is required in most catheters presently in use; provides all the benefits of bloodless catheterization and minimizes contamination by the pre-hookup of the intravenous unit; provides easy insertion into the patient without assistance by an aid; allows the addition of medicaments to the system without penetration of the rubber connecting tubing as presently is the practice, and thus eliminates the danger of microscopic rubber particles being intoduced into the body. This invention also eliminates the need to disconnect the catheter from the intravenous unit to administer medicaments, if and when desired.

Terms such as "left", "right", "up", "down", "bottom", "top", "front", "back", "in", "out" and the like are applicable to the embodiments shown and described in conjunction with the drawing. These terms are merely for the purposes of description and do not necessarily apply to the position in which the rotatable assembly for a flexible catheter may be constructed or used.

While particular embodiments of the rotatable assembly have been shown and described it is to be understood the invention is not limited thereto since modifications may be made within the scope of the accompanying claims and protection is sought to the broadest extent the prior art allows.

What is claimed is:

1. A rotatable tub assembly attachable to a single-channeled intracorporeal catheter, said assembly having a receiving socket for connection to the distal end of a fluid conducting system for feeding, injecting and draining, said assembly for use with a catheter member of flexible tubing having its intermediate portion formed with a relatively constant bore, said catheter having a distal end of tapered configuration and having its other end secured in a fluid-tight manner to a hub, said rotatable hub including: (a) a hub portion having a circular receiving recess formed therein and a connecting passageway from said recess and adapted to connect with the bore in the flexible catheter; (b) a rotatable member having a substantially circular portion mountable in said circular receiving recess in a fluid-tight manner and in said recess movable to two limits of rotation, this rotatable member having two passageways therethrough with each passageway in a plane generally normal to the axis of rotation of the movable member, a first passageway in alignment with the bore in the catheter when the rotatable member is in a first limit of movement and a second passageway having a flow connection with said catheter bore when the movable member is turned to the other limit of movement in said recess; (c) a hub portion formed in and on the rotatable member and extending exterior of said circular portion, this hub portion having a tapered socket formed therein, this socket adapted to receive and retain an end of a fluid conductor such as an intravenous fluid tubing and the like, the inner end of this socket flow connected to the second passageway, and (d) means for retaining the circular portion of the rotatable member in the circular recess formed in the hub portion of the rotatable assembly, the rotatable member when in the first position having the first passageway aligned with the bore of the catheter providing a substantially straight passageway through the catheter hub and assembly for the mounting therein of a needle which may be used to assist venipuncture and placement of the catheter in the body of the patient, the second passageway when the rotatable member is in the first position having its distal end closed to fluid flow by a portion of the wall of the circular recess and with the rotatable member at the second limit of movement this second passageway is in flow connection with the bore of the catheter and the ends of the first passageway formed in the circular portion of the rotatable member are moved from in way of a fluid flow to the catheter.

2. A rotatable assembly as in claim 1 in which the hub portion of the assembly has a tapered extending end sized and adapted for mounting and seating in a receiving socket of a flexible catheter.

3. A rotatable assembly as in claim 1 in which the hub portion of the assembly is integral with and also provides said hub of the flexible catheter.

4. A rotatable assembly as in claim 1 in which the hub portion is formed with a circular recess open to one side for the mounting therethrough and therein of the circular portion of the rotatable member and providing therewith a circular skirt which extends more than one-half around the recess with the ends of the skirt providing the limits to the movement of the rotatable member in the circular recess.

5. A rotatable assembly as in claim 4 in which the circular recess is tapered with the larger diameter toward the open side, this rotatable member having a like-sized and compatible taper which when mounted in the recess is a close sliding fit and the means for retaining the circular portion of the rotatable member in said recess is a shoulder portion formed in the hub portion at the outer portion of the recess and disposed to engage the outer portion of the rotatable member and retain this member in a seated condition in the recess.

6. A rotatable assembly as in claim 4 in which the circular recess is formed with two conical tapered portions, the larger extent of these portions being toward the midportion of the recess, one taper diminishing toward the open side of the recess, the circular portion of the rotatable member being inserted through the open side of the recess, the rotatable member having like-sized and compatible tapers when the rotatable member is seated in the recess, the two tapered surfaces providing a close sliding fit and a positioning means whereby the rotatable member is seated at the desired position in the recess, this outer taper of the recess as it diminishes from the midportion toward the open side providing the means for retaining the circular portion of the rotatable member in the circular recess formed in the hub portion.

7. A rotatable assembly as in claim 1 in which the hub portion is formed with the circular recess open to the rear with both sides of the hub portion joining to provide a circular skirt which extends more than half the distance around the recess, the recess having a contoured surface which is compatible and like-sized for the circular portion of the rotatable member which is inserted through this rear opening to the recess.

8. A rotatable assembly as in claim 7 in which the contoured surfaces on the periphery of the circular portion of the rotatable member and the circular recess in the huhb is arcuate in a transverse direction.

9. A rotatable assembly as in claim 1 in which a knob portion is formed on the rotatable member and a receiving detent is formed in the skirt portion of the hub, the knob when seated in this detent establishing and retaining the rotatable member in the second fluid-flow condition.

10. A rotatable assembly as in claim 1 in which a filter is mounted in said fluid-flow passageway formed in the circular portion of the hub and the filter is not penetrated by a needle.

11. A rotatable assembly as in claim 10 in which the filter is at the end of the passageway away from the socket in which is received the fluid-flow conductor.

12. A rotatable assembly as in claim 10 in which the filter is at the end of the passageway forming and connecting with the socket in the extending hub portion of the movable member.

13. A rotatable assembly as in claim 1 in which the passageway in and through the rotary member for the passage of the needle is by-passed by the second passageway which is provided for fluid flow.

14. A rotatable assembly as in claim 13 in which there is provided a transverse flow enlargement formed in the wall of the recess and connecting with the bore of the flexible catheter and the end of the passageway for fluid in the rotatable member is compatibly formed to mate with the transverse enlargement to provide a fluid flow from the connected tubing to the catheter when and as the rotatable member is moved to the fluid flow second position.

* * * * *